United States Patent [19]

Swiantek et al.

[11] Patent Number: 5,782,829
[45] Date of Patent: Jul. 21, 1998

[54] RESECTOSCOPE ELECTRODE ASSEMBLY AND METHODS OF USE

[75] Inventors: Philip Swiantek, Williamsville, N.Y.; James Muehleisen, Southampton, N.J.; Peter A. Manzie, Berwyn; Robert Baker, Barrington, both of Ill.

[73] Assignee: Northgate Technologies Incorporated, Elgin, Ill.

[21] Appl. No.: 568,130

[22] Filed: Dec. 6, 1995

[51] Int. Cl.⁶ .................................................. A61B 17/39
[52] U.S. Cl. .................................................. 606/46; 606/49
[58] Field of Search .................................... 606/46, 49

[56] References Cited

U.S. PATENT DOCUMENTS

| | | |
|---|---|---|
| D. 320,446 | 10/1991 | Grossi et al. |
| 4,060,087 | 11/1977 | Hiltebrandt et al. |
| 4,726,370 | 2/1988 | Karasawa et al. |
| 4,917,082 | 4/1990 | Grossi et al. |
| 4,955,884 | 9/1990 | Grossi et al. |
| 5,007,907 | 4/1991 | Nishigaki et al. |
| 5,196,011 | 3/1993 | Korth et al. |
| 5,267,994 | 12/1993 | Gentelia et al. |
| 5,423,813 | 6/1995 | Kaiser et al. |
| 5,486,173 | 1/1996 | Vancaillie |
| 5,549,605 | 8/1996 | Hahnen |
| 5,569,244 | 10/1996 | Hahnen ............................ 606/46 |
| 5,582,610 | 12/1996 | Grasso et al. ..................... 606/46 |
| 5,634,924 | 6/1997 | Turkel et al. |

OTHER PUBLICATIONS

"Vaporizing; Cutting Loops and Other Electrodes For Urology and Gynecology", *Nortech*, Order Sheet No. 80–16501–1 Rev. A., 1995.

*Primary Examiner*—Lee S. Cohen
*Attorney, Agent, or Firm*—BrinksHofer Gilson & Lione

[57] ABSTRACT

An improved electrode assembly for a resectoscope and methods for use thereof. The electrode assembly includes at least one electrical lead that connects at a proximal end via a handle of the resectoscope to an electrosurgical generator to receive electrical power. The electrode assembly further includes an electrode tip at a distal end. The electrode tip has a non-rotating, relatively flat, working surface that extends in a longitudinal direction. The tip can be used for ablation or coagulation by using the working surface. The tip includes an edge that can be used for cutting. The working surface includes a pattern that enhances generation of a current therefrom. The electrode tip is versatile so that the same tip can be used for cutting, vaporizing, ablating, and coagulating.

40 Claims, 3 Drawing Sheets

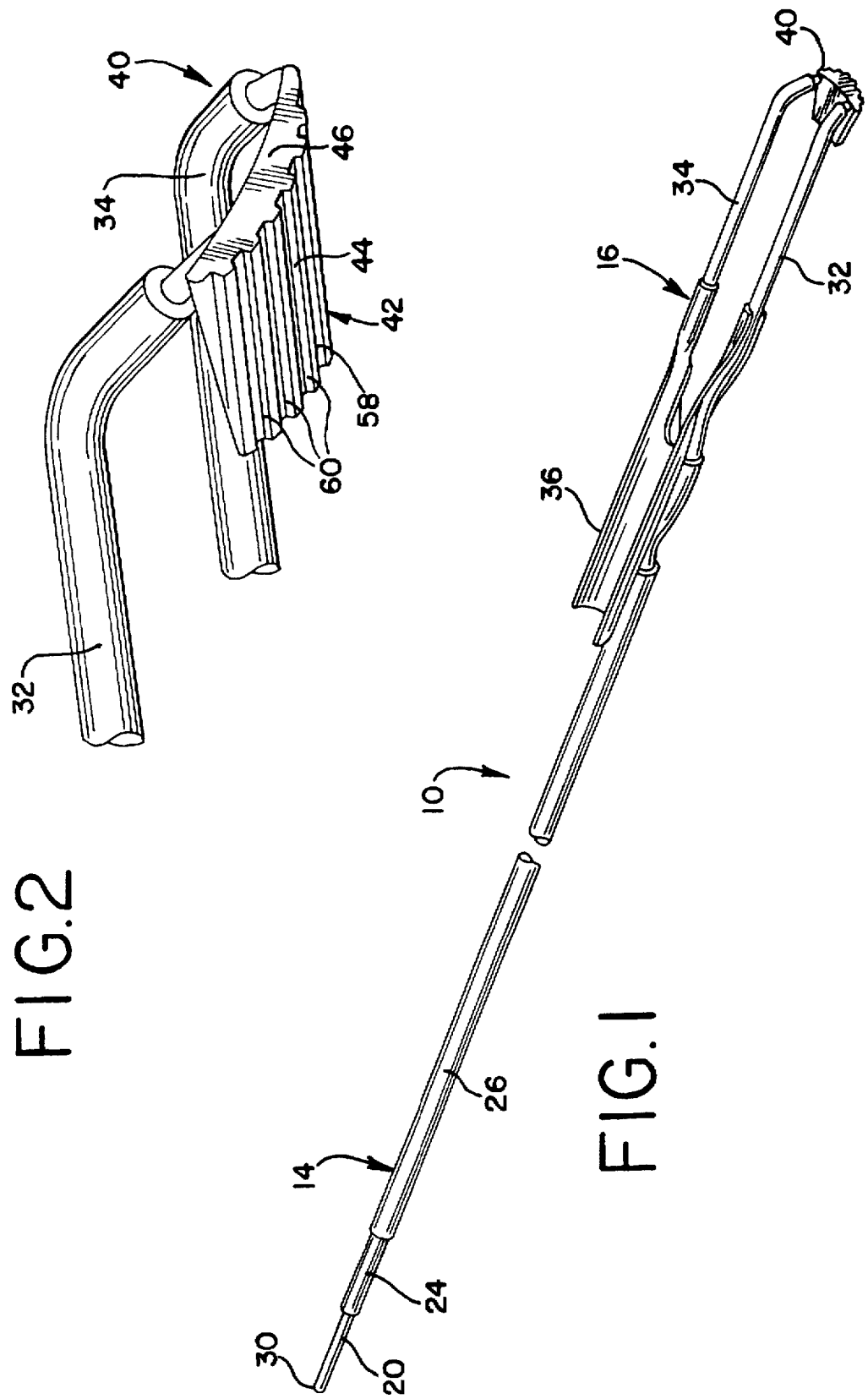

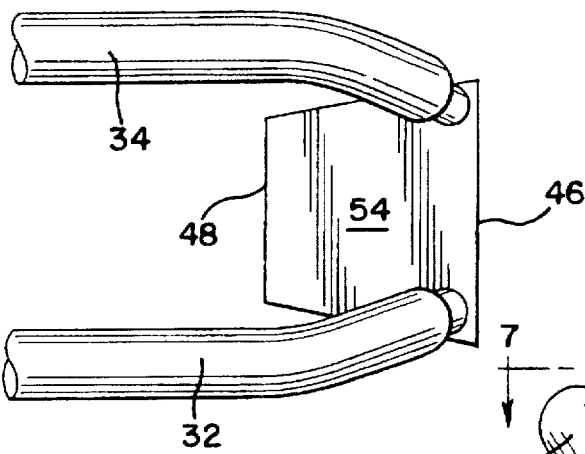
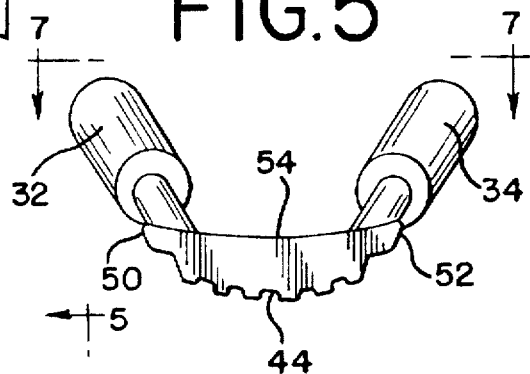
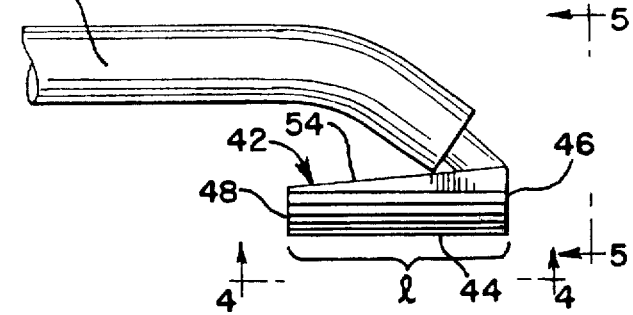
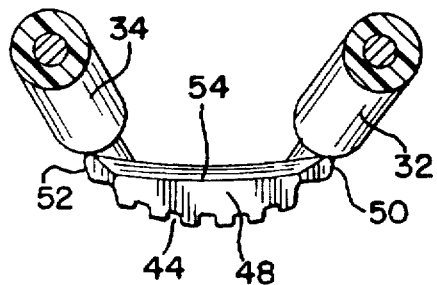
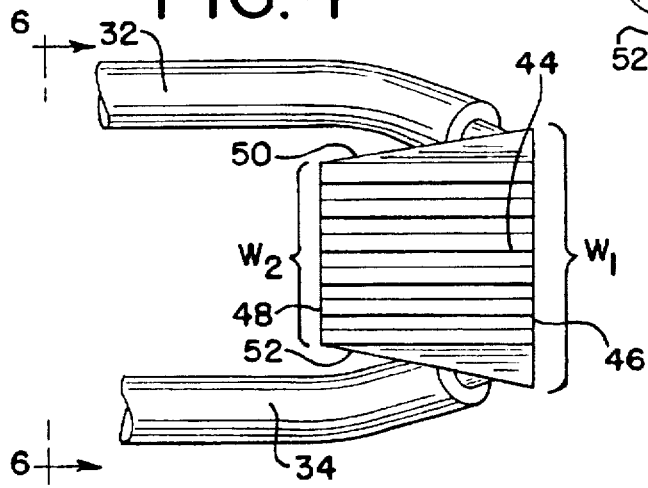

RESECTOSCOPE ELECTRODE ASSEMBLY AND METHODS OF USE

BACKGROUND OF THE INVENTION

The present invention relates to resectoscopes and methods of use thereof, and more particularly, the present invention relates to an improved electrode assembly apparatus for an electrosurgical resectoscope and methods for use thereof.

Electrosurgical resectoscopes are used for transurethral and gynecological surgical procedures. Conventional electrosurgical resectoscopes include a handle, a telescope for viewing the surgical site and an electrode assembly that can be used for performing surgical procedures. A proximal portion of the electrode assembly is formed of an elongate conductor surrounded by an insulative sheath. A distal portion of the electrode assembly is typically formed by a pair of insulated wire leads. The proximal ends of the wire leads are connected to the distal end of the elongate conductor of the proximal portion of the electrode assembly. In one type of electrode assembly used for cutting, the distal ends of the leads are connected together in a wire loop. The wire loop is orthogonal to the axial direction of the electrosurgical resectoscope.

The resectoscope handle includes a connection for a cable that connects to an electrosurgical generator to receive power therefrom. The electrode assembly fits into a connection in the resectoscope handle to receive power from the generator. The electrosurgical generator provides electrical energy at power levels that are controllable by the physician.

Electrosurgical resectoscopes can be used for cutting, coagulating, or ablating. As mentioned above, in one type of electrode assembly for a conventional electrosurgical resectoscope, the wires at a distal end of the electrode assembly form a loop. The loop is used for cutting tissue under observation with the telescope. Other types of electrode assembly tips have been designed for use with electrosurgical resectoscopes. For example, one type of tip is formed of a solid sphere and another type of tip has a rotating barrel.

Conventional electrosurgical resectoscopes have numerous advantages. For example, conventional electrosurgical resectoscopes are relatively easy and economical to use compared to other types of surgical instruments, such as laser-based surgical tools. However, there are several aspects of conventional electrosurgical resectoscopes that limit their usefulness. For example, electrode assemblies are not relatively versatile. With a conventional electrosurgical resectoscope, if the physician desires to perform different types of procedures, such as cutting a tissue to obtain a sample and then ablating the area, the physician generally has to withdraw the electrosurgical resectoscope to replace the electrode assembly with another electrode assembly that has a different type of tip. Another disadvantage is that the electrode assembly tip can become clogged with tissue during use, thereby requiring the physician to remove the entire electrosurgical resectoscope to clean the tip of the electrode assembly.

Accordingly, there is a need for an improved electrosurgical resectoscope electrode assembly.

SUMMARY OF THE INVENTION

To achieve the foregoing and other objectives and in accordance with the purposes of the present invention, there is provided an improved method and means for an electrode assembly for an electrosurgical resectoscope. The electrode assembly includes at least one electrical lead that connects at a proximal end via a handle of the electrosurgical resectoscope to an electrosurgical generator to receive electrical power therefrom. The electrode assembly further includes an electrode tip at a distal end. The electrode tip has a non-rotating, relatively flat, working surface that extends in a longitudinal direction. The electrode tip can be used for ablation or coagulation by using the working surface. The electrode tip includes an edge that can be used for cutting. The working surface includes a pattern that enhances generation of a current therefrom. The electrode tip is versatile so that the same tip can be used for cutting, vaporizing, ablating, and coagulating.

BRIEF DESCRIPTION OF THE DRAWINGS

FIG. 1 is a perspective view showing a first embodiment of an electrode assembly for electrosurgical resectoscope.

FIG. 2 is a close up perspective view of the tip of the electrode assembly of FIG. 1.

FIG. 3 is a side view of the tip of the electrode assembly shown in FIG. 2.

FIG. 4 is a bottom view of the electrode assembly taken along lines 4—4 of FIG. 3.

FIG. 5 is an end view of the electrode assembly taken along lines 5—5 of FIG. 3.

FIG. 6 is a sectional view of the electrode assembly taken long lines 6—6 of FIG. 5.

FIG. 7 is a top view of the electrode assembly taken along lines 7—7 of FIG. 4.

DETAILED DESCRIPTION OF THE PREFERRED EMBODIMENTS

Figure 8:
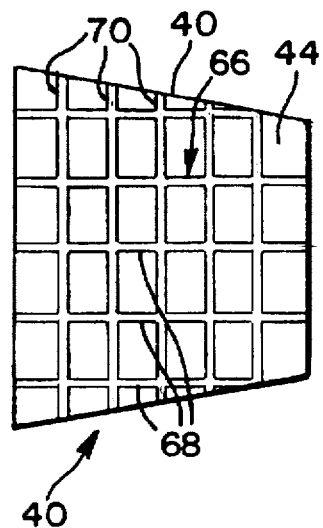
FIG. 8 is a view similar to FIG. 5 showing an alternate embodiment of a tip for an electrosurgical resectoscope electrode assembly.

FIG. 1 shows an electrode assembly 10 for an electrosurgical resectoscope. The electrode assembly 10 includes a proximal portion 14 and a distal portion 16. The proximal portion 14 includes a conductor 20 surrounded by an insulative plastic covering 24. The conductor 20 and covering 24 are enclosed by a rigid shaft 26. A proximal end 28 of the conductor 20 extends from the proximal end of the insulative covering 24 to form a connector pin which can be received in a jack on a conventional electrosurgical resectoscope handle (not shown). A proximal end of the insulative covering 24 extends from the proximal end of the rigid shaft 26.

The distal portion 16 of the electrode assembly 10 includes at least one, but preferably a pair of leads 32 and 34. Each of the leads includes an elongate conductor covered by an insulative covering. The proximal ends of the distal leads are connected electrically together to a distal end of the proximal conductor 20. The distal leads 32 and 34 diverge from each other distally of their proximal connection to the proximal conductor and extend parallel to each other to a distal end of the distal portion 16 of the electrode assembly 10. Located at the connection between the distal portion 16 and the proximal portion 14 is an elongate channel 36. The channel 36 is sized to receive the telescope portion (not shown) of the resectoscope as in a conventional resectoscope. The channel 36 is aligned to direct a resectoscope telescope between the parallel leads 32 and 34. At a distal end of the distal portion 16, the parallel leads angle downward to permit a telescope to extend distally past the distal end of the electrode assembly. The components of the electrode assembly described in detail so far may be manufactured according to conventional techniques using conventional materials.

The distal ends of the leads 32 and 34 both connect to a tip 40. The tip 40 is formed of an electrically conductive material so that the leads are connected together both mechanically and electrically. In this embodiment, the tip 40 is formed of a conductive block 42 having a wedge- or chip-like shape. The tip may be made of any suitable conductive material such as a nickel-silver alloy, stainless steel, or titanium.

Referring to FIGS. 2–7, the block 42 includes a working surface 44, a distal edge 46, a proximal edge 48, side edges 50 and 52, and an inner surface 54. As shown in FIG. 2, the working surface 44 is oriented in a direction away from the leads 32 and 34. The distal edge 46 of the tip 40 is located toward and faces the distal end of the electrode assembly 10 (FIG. 3). The proximal edge 48 is located opposite the distal edge 46 and faces toward the proximal end of the electrode assembly 10. The side edges 50 and 52 are located along horizontal or circumferential edges of the tip 40 (FIGS. 4–6). The inner surface 54 of the tip 40 is opposite the working surface 44 and oriented in a direction toward the leads 32 and 34 (FIGS. 3 and 7).

Referring to FIGS. 2 and 4, the working surface 44 is four-sided and has a trapezoidal shape. The working surface 44 extends a length, 1, in a longitudinal (or axial) direction. In the embodiment shown, the length, 1, of the working surface 44 is approximately 5 mm. The distal edge 46 has a width, $w_1$, of approximately 5 mm and the proximal edge 48 has a width, $w_2$, of approximately 4 mm.

As shown in FIG. 3, the working surface 44 is relatively straight in the longitudinal direction. As shown in FIG. 5, the working surface 44 preferably has a slight convex curvature in a horizontal (or circumferential) direction. This slight horizontal curvature of proximal edge 48 is provided so that the horizontal profile of the working surface 44 conforms generally to the shape of a conventional electrosurgical resectoscope sheath (not shown) through which the electrode assembly is introduced into the patient's body cavity. In a preferred embodiment, electrode assemblies may be provided in different sizes each having different working surface curvatures to accommodate different sizes of resectoscope sheaths.

As shown in FIG. 3, the tip 40 preferably has a wedge-like shape so that it is thicker at the distal edge 46 and thinner at the proximal edge 48. In one present embodiment, the tip is approximately 1.5 mm in thickness at the distal edge 46 and approximately 0.5 mm in thickness at the proximal edge 48. The distal edge 46 is relatively blunt and forms a surface that is relatively orthogonal to the working surface 44. The proximal edge 48 is slightly angled relative to the working surface forming a contoured surface.

As mentioned above, the leads 32 and 34 connect to the inner surface 54 of the tip 40. Specifically, the leads 32 and 34 connect to the inner surface close to the corners at which the side edges 50 and 52 meet the distal edge 46. This provides for current delivered to the tip 40 via the leads to flow relatively uniformly across the working surface 44. The leads 32 and 34 may be connected to the tip by any suitable means, such as soldering, welding, etc. The connection between the leads and the tip 40 is relatively rigid.

In a preferred embodiment, the working surface 44 of the tip 40 has a pattern 58 thereon. In the present embodiment, the pattern includes a plurality of grooves 60 or other surface configurations. These grooves 60 enhance the dissipation of current from the tip into the patient's tissue. The grooves 60 increase the surface area of the working surface 44. This is believed to cause a crowding of the current as it leaves the working surface and enters the patient's tissue. In a present embodiment, the working surface has a plurality or series of approximately six grooves and each groove is approximately 1 mm in width and 0.5 mm deep. The grooves 60 are evenly spaced and extend in the longitudinal direction from the distal edge 46 to the proximal edge 48.

The inner surface 54 is relatively smooth. In a present embodiment, it is preferred that the inner surface 54 have a concave contour that is similar to the contour of the working surface opposite thereto. The contour of the inner surface 54 provides for the tip having a relatively uniform thickness laterally and minimizes the mass of the tip.

The present embodiment of the electrode assembly is versatile and can be used by a physician for cutting, ablating, vaporizing, or coagulating. For example, to cut tissue, the physician assembles the resectoscope in a conventional manner and obtains access to the surgical site. The physician then advances the tip 40 around and distally past the tissue to be cut. Next, the physician sets the electrosurgical generator to a "cut" mode. Then, the physician brings the proximal edge 48 of the tip 40 into contact with the tissue to be cut and moves the electrode assembly in a proximal direction until the tissue is cut all the way through. The cut tissue may then be removed in a conventional way, such as by irrigating and flushing the area and in this manner a sample of tissue may be acquired.

The present embodiment of the electrode assembly can also be used for ablating or vaporizing. To use the present embodiment for ablating, the same electrode assembly can be used as described above. The physician adjusts the electrosurgical generator to a suitable power level. For example, the generator may be set to the "cut" mode with the power adjusted higher than 120 watts. A power setting as high as 260 watts may be used, although suitable ablating may be obtained at lower power levels. The physician then brings the working surface 44 of the tip 40 into contact with the area to be ablated. The working surface may be moved in any direction across the area to ablate the tissue in the area, as desired.

The present embodiment can also be used for coagulation. To coagulate an area, the physician sets the generator to the appropriate mode, such as the "coag" mode. The power level in this mode is relatively lower than in the "cut" mode. The physician brings the working surface 44 into contact with the area to be coagulated.

The electrode assembly as described above enables a physician to perform a variety of procedures with the same electrode assembly thereby obviating the need to withdraw the resectoscope to change the electrode tip. Thus, the present embodiment of the electrode assembly facilitates efficiency and may reduce the cost by eliminating the need to use a variety of electrode assemblies.

The present embodiment of the electrode assembly provides additional features. As mentioned above, in a present embodiment, the working surface 44 has pattern, such as grooves 60, which enhance current-crowding. During cutting, ablating, or coagulation procedures, it is possible that tissue may adhere to the tip. In the present embodiment, the working surface 44 has grooves that could become clogged by tissue during the procedure. The grooves 60 may be cleared by moving the working surface in a longitudinal direction across another surface. This other surface may be an end of the resectoscope shaft or even a portion of tissue in the patient. This clearing procedure may be done without removing the electrode assembly from the patient and may be done without applying power to the tip.

Figure 9:
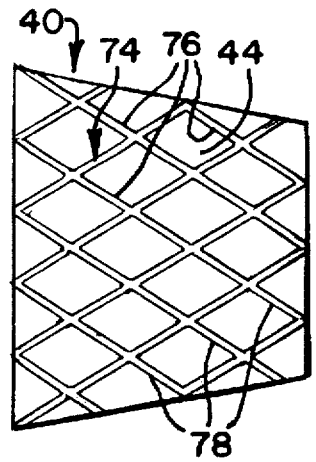
FIG. 9 is a view similar to FIG. 5 showing another alternate embodiment of a tip for an electrosurgical resectoscope electrode assembly.
Figure 10:
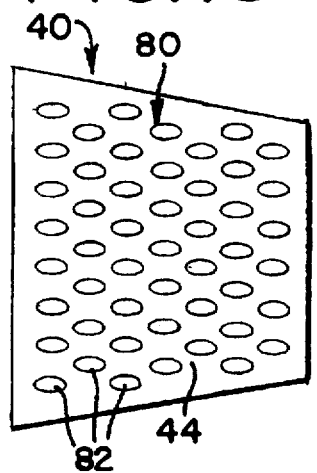
FIG. 10 is a view similar to FIG. 5 showing still another alternate embodiment of a tip for an electrosurgical resectoscope electrode assembly.

Alternative embodiments of the working surface 44 of the tip 40 are shown in FIGS. 8–10. In FIG. 8, the working surface 44 includes a groove pattern 66 that has longitudinal grooves 68 and laterally-extending grooves 70. This groove pattern 66 increases the surface area of the working surface 44 and may enhance the current crowding effect. FIG. 9 shows another embodiment of a groove pattern 74 for the working surface 44. In FIG. 9, the groove pattern 74 includes a first group 76 of parallel grooves that run diagonally across the working surface 44 and a second group 78 of parallel grooves that also run diagonally across the working surface 44. The first and second groups of grooves intersect each other, as shown. FIG. 10 shows another pattern 80 for the working surface 44. In FIG. 10, the working surface 44 includes a plurality of cavities 82. These cavities 82 increase the surface area of the working surface 44 to provide the current crowding effect. In addition to these patterns, the working surface may include other types of patterns, such as contours, irregularities, textures, or other types of non-smooth features, or may have other structure that enhances the distribution of current therefrom.

It is intended that the foregoing detailed description be regarded as illustrative rather than limiting and that it is understood that the following claims including all equivalents are intended to define the scope of the invention.

We claim:

1. A method of using a resectoscope wherein said resectoscope includes an electrode assembly with an electrode tip having a substantially flat, non-rotating working surface, comprising the steps of:
   operating the electrode assembly of the resectoscope at a first wattage;
   moving a proximal edge of said working surface into a region of tissue to be cut;
   moving the electrode tip in a proximal direction to sever the tissue;
   bringing the working surface against a region to be ablated; and
   operating the resectoscope to ablate the region.

2. The method of claim 1 wherein the ablation is performed with the same electrode assembly as the cutting.

3. The method of claim 1 further comprising the step of:
   acquiring a sample of tissue.

4. A method of using a resectoscope wherein said resectoscope includes an electrode assembly with an electrode tip having a substantially flat, non-rotating, working surface, comprising the steps of:
   operating the resectoscope at a first wattage;
   bringing an edge of the working surface into contact with a region;
   moving the working surface in a proximal direction across the region to cut all the way through tissue;
   changing the wattage; and
   bringing the working surface into contact with the region a second time.

5. The method of claim 4 further comprising the step of:
   after the step of bringing the working surface into contact with the region a second time, ablating the tissue of the patient.

6. The method of claim 5 wherein said step of ablating tissue of the patient comprises:
   bringing said substantially flat, non-rotating, working surface into contact with the tissue to be ablated.

7. The method of claim 4 further comprising the step of:
   after the step of bringing the working surface into contact with the region a second time, vaporizing the tissue of the patient.

8. The method of claim 7 wherein said step of vaporizing tissue of the patient comprises:
   bringing said substantially flat, non-rotating, working surface into contact with the tissue to be vaporized.

9. The method of claim 4 further comprising the step of:
   after the step of bringing the working surface into contact with the region a second time, coagulating the tissue of the patient.

10. The method of claim 9 wherein said step of coagulating tissue of the patient comprises:
    bringing said substantially flat, non-rotating, working surface into contact with the tissue to be coagulated.

11. The method of claim 4 wherein the step of bringing the working surface into contact with the region a second time is further characterized by the step of:
    moving the working surface across the region to ablate the region.

12. The method of claim 4 wherein the step of bringing the working surface into contact with the region a second time is further characterized by the step of:
    moving the working surface across the region to coagulate the region.

13. The method of claim 4 further comprising the step of:
    prior to the step of operating the resectoscope at a first wattage, setting a generator to which the resectoscope is coupled to a wattage of at least 120 watts.

14. The method of claim 4 wherein said working surface of said resectoscope includes longitudinally-extending grooves, and wherein said method further comprises the steps of:
    cleaning the working surface by moving the working surface in a longitudinal direction across a portion of the tissue of the patient without removing the electrode assembly from the patient.

15. The method of claim 4 further wherein the step of changing the wattage is further characterized as comprising:
    setting a power level to a relatively lower power level.

16. A method of using a resectoscope comprising the steps of:
    providing a resectoscope having an electrode assembly with an electrode tip with a distal edge, a proximal edge, a substantially flat, non-rotating, working surface extending from said distal edge to said proximal edge, and a pair of leads coupled to said tip close to said distal edge;
    performing a surgical cutting procedure on a patient with said resectoscope having said electrode assembly and performing another surgical procedure other than surgical cutting on the patient with said resectoscope having said electrode assembly without removing said resectoscope assembly from the patient to change said tip, comprising the steps of:
    operating the electrode assembly of the resectoscope at a first wattage;

moving the tip distally past a region of tissue to be cut;
bringing the proximal edge into contact with the tissue to be cut;
moving the electrode tip in a proximal direction to cut the tissue all the way through;
adjusting the resectoscope to another wattage; and
performing the other surgical procedure other than surgical cutting on the patient without removing said electrode assembly from the patient.

17. The method of claim 16 wherein said surgical procedure other than cutting comprises ablating tissue of the patient.

18. The method of claim 17 wherein said step of ablating tissue of the patient comprises:
bringing said substantially flat, non-rotating, working surface into contact with the tissue to be ablated.

19. The method of claim 16 wherein said surgical procedure other than cutting comprises vaporizing tissue of the patient.

20. The method of claim 19 wherein said step of vaporizing tissue of the patient comprises:
bringing said substantially flat, non-rotating, working surface into contact with the tissue to be vaporized.

21. The method of claim 16 wherein said surgical procedure other than cutting comprises coagulation.

22. The method of claim 21 wherein said step of coagulation comprises:
bringing said substantially flat, non-rotating, working surface into contact with the tissue to be coagulated.

23. The method of claim 16 further comprising the step of:
cleaning the working surface by moving the working surface in a longitudinal direction across a portion of the tissue of the patient without removing the electrode assembly from the patient.

24. The method of claim 16 further comprising the steps of:
irrigating and flushing the tissue to remove the tissue from the patient.

25. The method of claim 24 wherein said steps of irrigating and flushing are performed after the step of moving the electrode tip in a proximal direction to cut the tissue but before the step of performing the other surgical procedure other than surgical cutting.

26. The method of claim 16 further wherein the step of adjusting the resectoscope to another wattage further comprises:
setting a power level to a relatively lower power level.

27. A method of using a resectoscope comprising the steps of:
providing a resectoscope having an electrode assembly with an electrode tip with a distal edge, a proximal edge, a substantially flat, non-rotating, working surface extending from said distal edge to said proximal edge, and at least one lead coupled to said tip close to said distal edge to provide electrical current thereto from an electrosurgical generator, the method comprising the steps of:
setting the electrosurgical generator to a cutting mode;
moving the electrode tip distally past a region of tissue to be cut;
bringing the proximal edge into contact with the tissue to be cut;
moving the electrode tip in a proximal direction to cut the tissue all the way through;
adjusting the electrosurgical generator to another power level; and
while operating at said other power level, performing another surgical procedure other than surgical cutting on the patient without removing said electrode assembly from the patient.

28. The method of claim 27 further wherein the step of adjusting the electrosurgical surgical generator to another power level is further characterized as comprising:
setting the power level relatively lower.

29. A method of using a resectoscope comprising the steps of:
providing a resectoscope having an electrode assembly with an electrode tip with a distal edge, a proximal edge, a substantially flat, non-rotating working surface having longitudinally-extending grooves located thereon extending from said distal edge to said proximal edge, and at least one lead coupled to said tip close to said distal edge; and
performing a surgical cutting procedure on a patient with said resectoscope having said electrode assembly and performing another surgical procedure other than surgical cutting on the patient with said resectoscope having said electrode assembly without removing said resectoscope assembly from the patient to change said tip, comprising the steps of:
operating the electrode assembly of the resectoscope at a first wattage;
moving the tip distally past a region of tissue to be cut;
bringing the proximal edge into contact with the tissue to be cut;
moving the electrode tip in a proximal direction to cut the tissue all the way through;
adjusting the resectoscope to another wattage; and
performing the other surgical procedure other than surgical cutting on the patient without removing said electrode assembly from the patient.

30. The method of claim 29 wherein said surgical procedure other than cutting comprises ablating tissue of the patient.

31. The method of claim 30 wherein said step of ablating tissue of the patient comprises:
bringing said substantially flat, non-rotating, working surface into contact with the tissue to be ablated.

32. The method of claim 29 wherein said surgical procedure other than cutting comprises vaporizing tissue of the patient.

33. The method of claim 32 wherein said step of vaporizing tissue of the patient comprises:
bringing said substantially flat, non-rotating, working surface into contact with the tissue to be vaporized.

34. The method of claim 29 wherein said surgical procedure other than cutting comprises coagulation.

35. The method of claim 34 wherein said step of coagulation comprises:
bringing said substantially flat, non-rotating, working surface into contact with the tissue to be coagulated.

36. The method of claim 29 further comprising the step of:
cleaning the working surface by moving the working surface in a longitudinal direction across a portion of the tissue of the patient without removing the electrode assembly from the patient.

37. The method of claim 29 further comprising the steps of:
irrigating and flushing the tissue to remove the tissue from the patient.

38. The method of claim 37 wherein said steps of irrigating and flushing are performed after the step of moving the electrode tip in a proximal direction to cut the tissue but before the step of performing the other surgical procedure other than surgical cutting.

39. The method of claim 29 further wherein the step of adjusting the resectoscope to another wattage further comprises:

setting a power level to a relatively lower power level.

40. A method of using a resectoscope wherein said resectoscope includes an electrode assembly with an electrode tip having a substantially flat, non-rotating working surface, comprising the steps of:

operating the electrode assembly of the resectoscope at a first wattage;

moving a proximal edge of said working surface into a region of tissue to be cut;

moving the electrode tip in a proximal direction to sever all the way through the tissue;

changing the wattage;

bringing the working surface into contact against the region a second time; and operating the resectoscope to coagulate the region.

* * * * *

UNITED STATES PATENT AND TRADEMARK OFFICE
CERTIFICATE OF CORRECTION

PATENT NO.   : 5,782,829
DATED        : July 21, 1998
INVENTOR(S)  : Philip Swiantek et al.

It is certified that error appears in the above-identified patent and that said Letters Patent is hereby corrected as shown below:

<u>Title page,</u>
OTHER PUBLICATIONS, under "Attorney", please change "BrinksHofer" to -- Brinks Hofer --.

Signed and Sealed this

Eleventh Day of June, 2002

Attest:

JAMES E. ROGAN
Attesting Officer
Director of the United States Patent and Trademark Office